(12) United States Patent
Howell et al.

(10) Patent No.: US 7,305,896 B2
(45) Date of Patent: Dec. 11, 2007

(54) CAPILLARY FILL TEST DEVICE

(75) Inventors: Steven Howell, Northants (GB); James Troke, Beds (GB)

(73) Assignee: Inverness Medical Switzerland GmbH, Zug (CH)

( * ) Notice: Subject to any disclaimer, the term of this patent is extended or adjusted under 35 U.S.C. 154(b) by 66 days.

(21) Appl. No.: 10/930,717

(22) Filed: Aug. 31, 2004

(65) Prior Publication Data
US 2005/0229722 A1    Oct. 20, 2005

Related U.S. Application Data

(60) Provisional application No. 60/509,093, filed on Oct. 6, 2003.

(30) Foreign Application Priority Data
Sep. 1, 2003    (GB)    ................... 0320470.8

(51) Int. Cl.
G01N 1/12    (2006.01)
A61B 5/15    (2006.01)

(52) U.S. Cl. .................. 73/864.02
(58) Field of Classification Search .............
73/864.01–864.02, 864.72; 422/100, 102–103, 422/947
See application file for complete search history.

(56) References Cited

U.S. PATENT DOCUMENTS

| | | | |
|---|---|---|---|
| 3,406,573 A * | 10/1968 | Burke | 73/864.02 |
| 3,603,156 A * | 9/1971 | Konkol | 73/864.02 |
| 3,952,599 A * | 4/1976 | Ayres | 73/864.02 |
| 5,141,868 A | 8/1992 | Shanks et al. | 435/287.9 |
| 5,278,079 A * | 1/1994 | Gubinski et al. | 73/864.02 X |
| 5,975,153 A | 11/1999 | Hill et al. | 141/31 |
| 6,001,229 A | 12/1999 | Ramsey | |
| 6,098,471 A * | 8/2000 | Berndtsson et al. | 73/864.87 |
| D435,300 S | 12/2000 | Bhullar et al. | |
| D441,089 S | 4/2001 | Bhullar et al. | |
| 6,232,129 B1 * | 5/2001 | Wiktor | 73/864.02 X |
| 6,270,637 B1 | 8/2001 | Crismore et al. | |
| 6,387,328 B1 * | 5/2002 | Berndtsson | 422/100 X |
| 6,413,395 B1 | 7/2002 | Bhullar et al. | |

(Continued)

FOREIGN PATENT DOCUMENTS

EP    0 280 347 A1    8/1988

(Continued)

OTHER PUBLICATIONS

International Search Report for PCT/GB2004/003683, mailed Dec. 22, 2004.

Primary Examiner—Thomas P. Noland
(74) Attorney, Agent, or Firm—Scott E. Kamholz; Foley Hoag LLP

(57) ABSTRACT

A device for receiving a sample of liquid, such as a sample of bodily liquid which is to be subjected to further analysis, may include a body having at least a major surface and a minor surface. A sample-receiving chamber may be located in the body and may have an inlet end which opens into the major and minor surfaces of the body. A conduit may be located in the body, extending from the outlet end of the chamber, and may be arranged so as to allow the liquid to pass from the outlet end into the conduit by capillary action.

10 Claims, 7 Drawing Sheets

U.S. PATENT DOCUMENTS

| | | |
|---|---|---|
| 6,428,664 B1 | 8/2002 | Bhullar et al. |
| 6,447,657 B1 | 9/2002 | Bhullar et al. |
| 6,488,828 B1 | 12/2002 | Bhullar et al. |
| 6,540,890 B1 | 4/2003 | Bhullar et al. |
| 6,557,427 B2 | 5/2003 | Weigl et al. |
| 6,645,359 B1 | 11/2003 | Bhullar et al. |
| 6,662,439 B1 | 12/2003 | Bhullar |
| 6,707,554 B1 | 3/2004 | Miltner et al. |
| 6,755,949 B1 | 6/2004 | Bhullar et al. |
| 6,767,440 B1 | 7/2004 | Bhullar et al. |
| 6,814,843 B1 | 11/2004 | Bhullar et al. |
| 6,814,844 B2 | 11/2004 | Bhullar et al. |
| 6,866,758 B2 | 3/2005 | Bhullar et al. |
| 6,911,621 B2 | 6/2005 | Bhullar et al. |
| 7,063,774 B2 | 6/2006 | Bhullar et al. |
| 7,073,246 B2 | 7/2006 | Bhullar et al. |
| 7,128,876 B2 * | 10/2006 | Yin et al. ............ 422/100 |
| 2001/0036424 A1 * | 11/2001 | Takahashi et al. ....... 422/100 |
| 2002/0160520 A1 | 10/2002 | Orloff et al. ............. 436/72 |
| 2003/0028125 A1 | 2/2003 | Yuzhakov et al. ........ 600/583 |
| 2003/0047011 A1 * | 3/2003 | Diermann et al. ...... 73/864.02 |
| 2003/0070498 A1 * | 4/2003 | Ohyama et al. ..... 73/864.02 X |
| 2004/0197231 A1 | 10/2004 | Katsuki et al. .......... 422/68.1 |
| 2006/0233671 A1 * | 10/2006 | Beard et al. ............ 422/100 |
| 2006/0233672 A1 * | 10/2006 | Reed ..................... 422/100 |
| 2006/0233673 A1 * | 10/2006 | Beard et al. ............ 422/100 |
| 2007/0003444 A1 * | 1/2007 | Howell et al. ........... 422/100 |
| 2007/0014694 A1 * | 1/2007 | Beard et al. ............ 422/100 |

FOREIGN PATENT DOCUMENTS

| | | |
|---|---|---|
| EP | 1 284 121 A2 | 2/2003 |
| JP | 2000-232972 | 8/2000 |
| WO | WO 03/010530 A1 | 2/2003 |

* cited by examiner

Section X-X

Section X-X

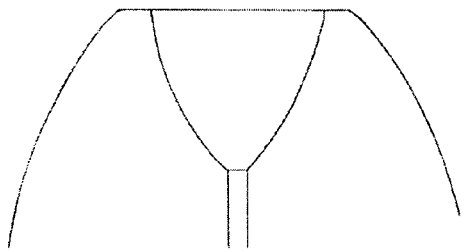
FIG. 5A
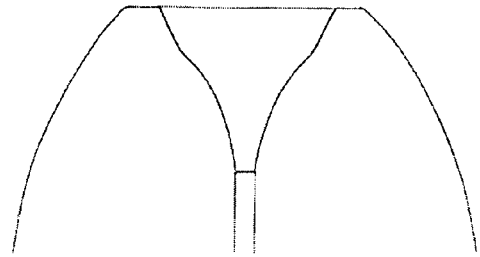
FIG. 5B
FIG. 6
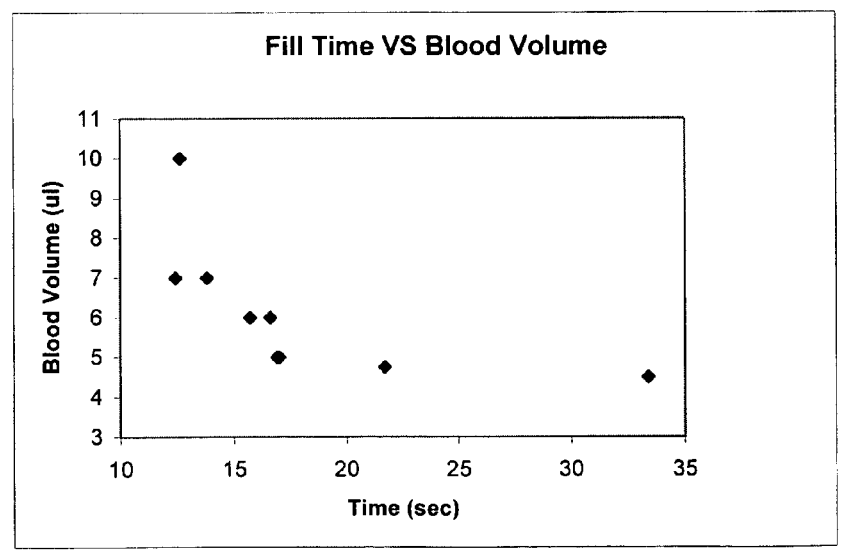

SECTION X-X

CAPILLARY FILL TEST DEVICE

CROSS-REFERENCE TO RELATED APPLICATION

This application claims the benefit of U.S. Provisional Pat. App. Ser. No. 60/509,093, filed Oct. 6, 2003, the contents of which is hereby incorporated herein by reference.

BACKGROUND

Known fluid sample-receiving devices used for blood glucose monitoring take up finger stick blood very rapidly. This is not a problem, as the measurement undertaken does not require actively moving or capillary-driven blood.

However, there exists a problem with the application of finger prick blood onto diagnostic devices for use where the sample is required to be actively moved or capillary driven along the device.

SUMMARY

Devices are disclosed for receiving a sample of liquid, and in particular, but not exclusively, for receiving a sample of bodily liquid such as blood so that it can be subjected to an assay.

In an embodiment, a device for receiving a sample of liquid may include a body, a sample-receiving recess, and a conduit. The body may have at least opposed first and second major outwardly facing surfaces each defining a periphery, and a peripheral wall joining the peripheries of the major surfaces. A conduit may extend from the outlet of the recess into an interior of the body between the first and second major surfaces. The conduit may be arranged so as to allow the liquid to pass from the outlet into the conduit by capillary action, and the conduit may have a maximum width no greater than the width of the recess at the outlet end and a conduit axis that runs along its length. A sample-receiving recess may be located inside of the first major surface of the body and may be defined in part by a surface substantially parallel to the first major surface and being outwardly exposed along an axis perpendicular to the conduit axis. The recess may include an inlet defined in part by the peripheral wall and an outlet spaced apart from the peripheral wall within the body, and a width that decreases from the inlet end to the outlet end.

In an embodiment, a device for receiving a sample of liquid may include a body having at least a major surface and a minor surface, a sample-receiving chamber located in the body and having an inlet end which opens into the major and minor surfaces of the body, and a conduit located in the body and extending from the outlet end of the chamber, the conduit being arranged so as to allow the liquid to pass from the outlet end into the conduit by capillary action.

In an embodiment, a device for receiving a sample of liquid may include a body having at least an end wall, a generally V-shaped sample-receiving chamber located in the body and having an inlet end which opens into the end wall of the body, and a conduit located in the body and extending from the outlet end of the chamber, the conduit being arranged so as to allow the liquid to pass from the outlet end into the conduit by capillary action.

BRIEF DESCRIPTION OF THE DRAWINGS

FIGS. 5a and b are plan views of two embodiments of devices;
FIG. 6 is a graph plotting fill time against the volume of whole blood added to a device.

DETAILED DESCRIPTION

Figure 1:
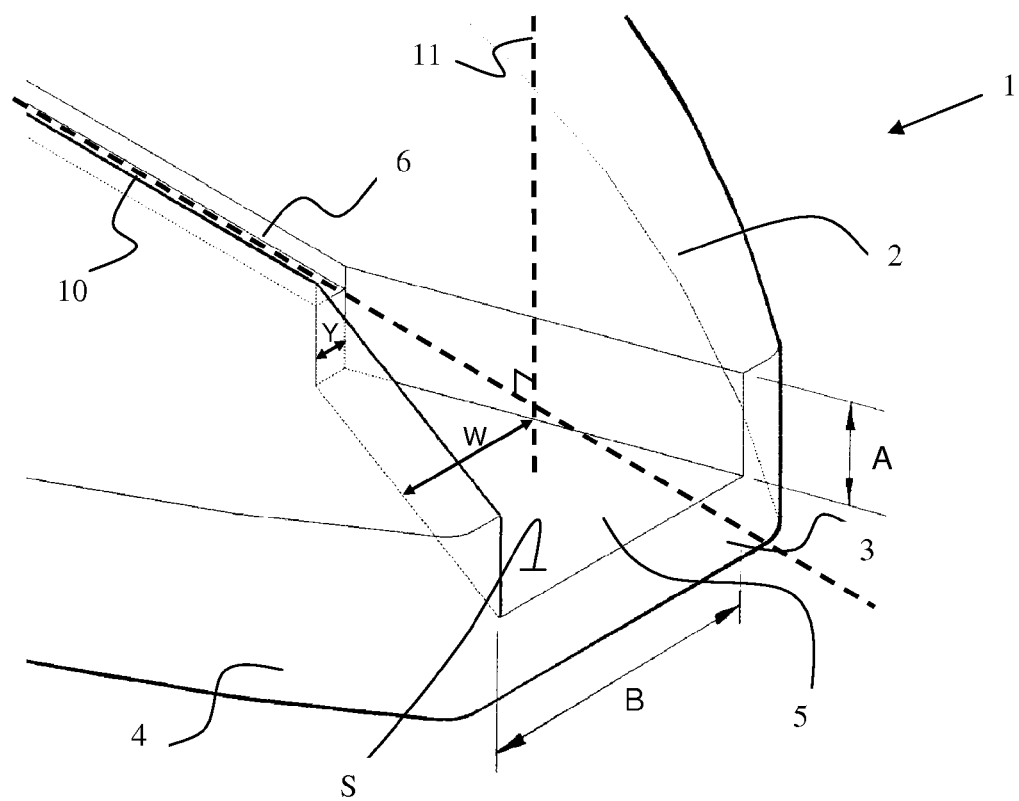
FIG. 1 is a partial isometric view of one embodiment of a device.
Figure 2:
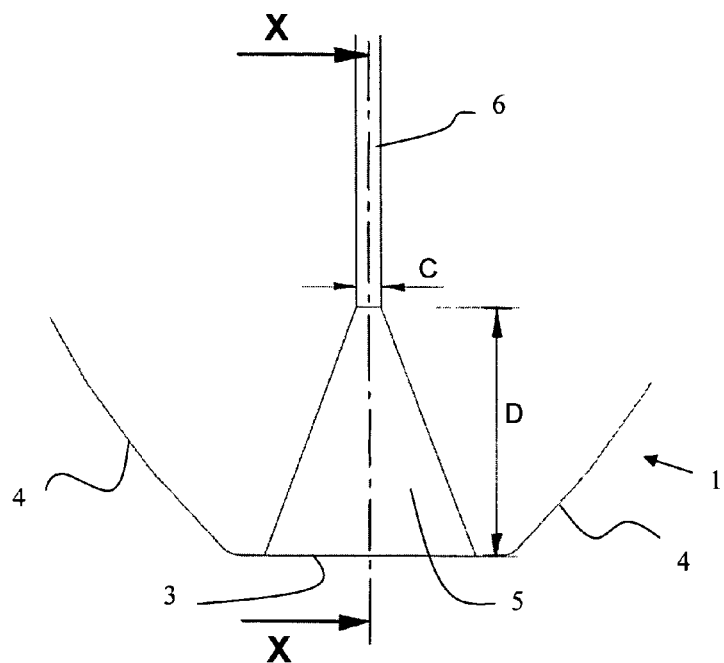
FIG. 2 is a plan view of the device of FIG. 1.
Figure 3:
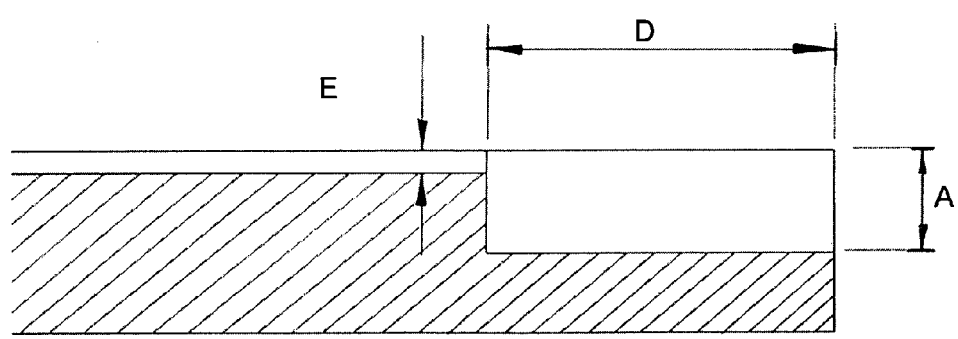
FIG. 3 is a section along the line X-X in FIG. 2.
Figure 4:
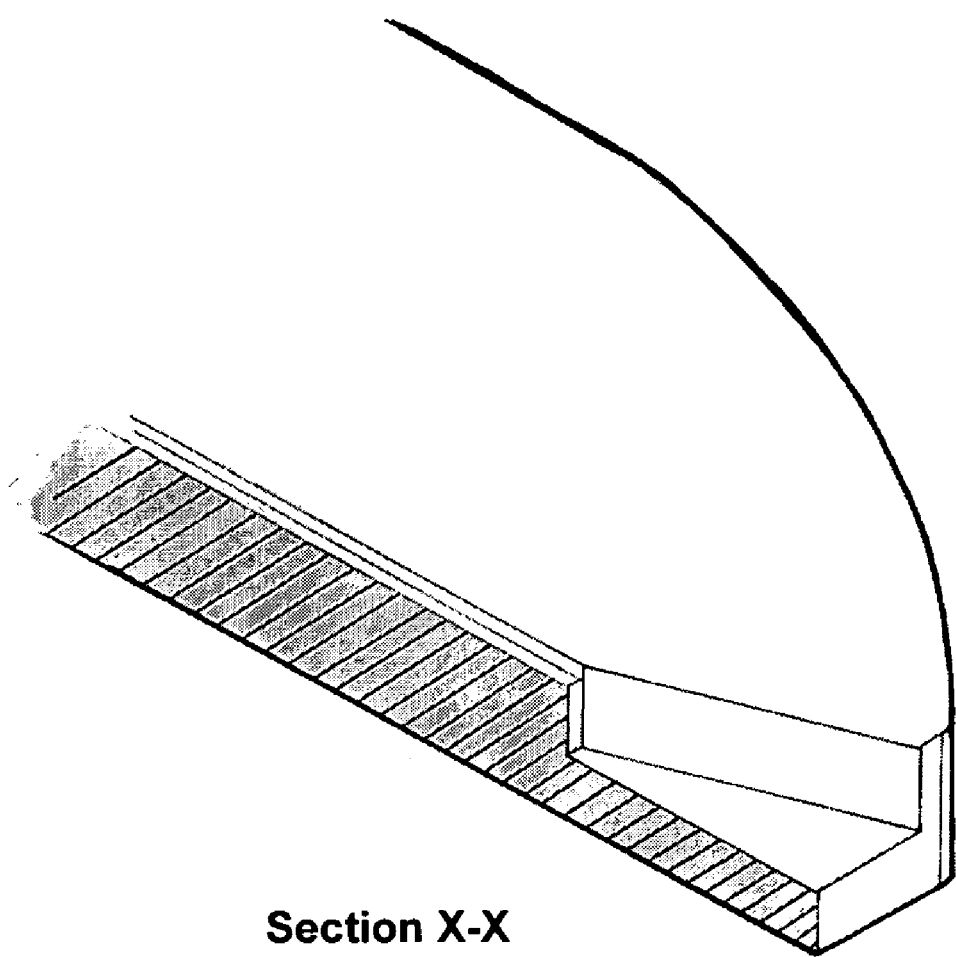
FIG. 4 is an isometric view of a section along the line X-X in FIG. 2.

A user may deposit a liquid sample into or onto the device at the sample-receiving chamber. The sample-receiving chamber may include an inlet end, such as a notch, that opens onto two surfaces of the device. This geometry can provide an easy target for a user to position the source of fluid, such as a pricked finger expressing a drop of blood, onto the device. The device can facilitate delivery of the liquid into the conduit, for example to allow an assay to be performed at another area of the device. This can be particularly helpful for diagnostic devices for blood samples where the assay result is not produced instantly, for example immunoassays requiring immunobinding of reagents to occur or biological enzyme reactions which link the measurement of blood clotting time. Safe delivery of the fluid into the conduit can also facilitate processing of the sample where diagnosis or assay has to be carried out remote from the sample-receiving chamber.

The sample-receiving chamber may act as a liquid reservoir which can thereafter supply the rest of the device with sufficient liquid even in the absence of the user maintaining contact with the device and removes the need for the user to maintain constant contact with the device during the filling process. This is especially advantageous for older people who might find it difficult to maintain constant contact with a device which may be of small dimensions. Furthermore, it reduces the possibility of device malfunction as removal of the liquid source at any time during filling may result in underfilling or the introduction of air bubbles.

The chamber can be included in devices which have a filling time greater than the time taken for the user to merely present the source of liquid to the device and to then remove it, for example a filling time of one second or more.

A disclosed device may be for use in chemical (especially biochemical or clinical) test procedures, often known as a capillary fill test device. Capillary fill test devices are typically used in combination with a second device, typically an electronic instrument designed to detect the existence, or the extent of, a predetermined interaction of the liquid sample, or one or more analytes in the liquid sample, with one or more other components of the device. Such components may be an electrode structure and/or one or more fluid-interactive or analyte-reactive compositions. The electronic instrument may be used to assess the sample liquid in the device, most typically by photometric or electrometric techniques after a predetermined sample reaction period. Capillary fill devices are often designed to be positioned in the electronic instrument before the device is loaded with the fluid sample. When the capillary fill device is properly positioned in the instrument, the sample-receiving chamber is external to the instrument and accessible to the user, and the area of the device where analysis takes place is located in electrical or phototransmissive/photoreflective communication with a sensor element capable of detecting and reporting a condition or change of condition of the liquid after or during a predetermined time period. A volume of test liquid may be delivered to the sample-receiving chamber to be drawn by capillary action (and possibly other forces) into and through the conduit and into the area of the device where analysis takes place. The instrument can be equipped with sensors to detect the flow of the test liquid through the conduit; optionally the instrument can be designed to use such detected flow to initiate a test sequence. In some liquid testing applications, for example, in certain instruments designed for use with capillary fill devices for determining coagulation characteristics of blood, the rate of flow of the liquid through the capillary flow conduit may be sensed and used as a parameter in the test sequence. In such testing applications, the conduit serves additionally to provide means for measuring flow characteristics, i.e., viscosity, of the test liquid as it is delivered to the test area.

The body of the device may be a generally rectilinear strip, as may be conventional for capillary test devices. Such strips may have end walls, side walls and/or top and bottom surfaces or parts thereof which are not parallel to each other. Alternatively, it may be cylindrical, wedge-shaped, disc-shaped, or any other convenient shape, provided that it has major and minor surfaces into which the inlet end of the sample-receiving chamber opens.

The inlet end of the sample-receiving chamber opens into the major and minor external surfaces of the body. The major and minor surfaces may be generally perpendicular to each another, and the minor surface may have a significantly smaller surface area than the major surface. The minor surface may be an end or side wall and the major surface may be a top surface (when the body is a rectilinear strip or wedge- or disc-shaped for example). In such instances, the sides of the device cannot be considered to be major surfaces. In one embodiment, the minor surface may be an end wall and the major surface may be an outer surface (when the body is cylindrical for example). Regardless of the shape of the body, the opening of the inlet end may be preferably continuous in the major and minor surfaces.

The portion of the sample-receiving chamber which opens into the minor surface may be less than the portion which opens into the major surface. For example, the area of the chamber opening onto the major surface may be 1.3 to 3 times, in one embodiment 1.6 times, the area of the chamber opening into the minor surface.

The sample-receiving chamber may taper from the inlet end to the outlet end, and may be generally, V- or U-shaped. For example, the width of the inlet end may be approximately 10-15 times the width of the outlet end, and may be 0.5-1.5 times the length of the sample-receiving portion.

The conduit may be arranged so as to allow the liquid sample to move by capillary action, although other forces can act on the liquid such as hydrostatic pressure and/or positive displacement to cause it to move along the conduit. For example, when viewed in section perpendicular to the longitudinal axis, the maximum dimension of the conduit may be less than 0.5, 0.4 or 0.3 mm. In one embodiment, the maximum dimension may be in the range of from 0.25 to 0.3 mm and may be about 0.28 mm. The conduit may have a Reynolds number less than about 2000 (i.e., the Reynolds lower critical number for pipe flow), this number being calculated according to the formula:

$$R_e = \frac{\rho V d}{\eta}$$

where $R_e$=Reynolds number, $\rho$=Fluid density, V=Fluid velocity, d=length scale, and $\eta$=dynamic viscosity. A Reynolds number of 2000 or less will cause the conduit (which may be considered to be a microstructure or microchannel) to be filled passively by surface tension (capillarity) alone.

At least the sample-receiving chamber and the conduit are conveniently coated with a hydrophilic coating, which may be on any or all of the walls thereof. The coating may provide a contact angle of 90° or less, 30° or less, or 200 or less. The contact angle may be in the range of from 5 to 15° and may be 11°. It may provide a contact angle of 110° provided that it is applied only on one wall. The contact angle may be determined as described at page 46 of "Fundamental and Applications of Microfluidics", Nguyen & Werely, Artech House, 30 Sep. 2002, ISBN 1580533434.

The liquid to be sampled can be any liquid. In a preferred embodiment, the liquid may be a bodily liquid, such as whole blood, plasma, interstitial fluid, cerebrospinal fluid (CSF), urine, serum, saliva, tears and sweat.

A disclosed device may be used to receive blood which may be subjected to the measurement of blood coagulation and/or other hemostasis measurements, such as prothrombin times. They may also be used in to receive bodily liquids which are subjected to immunoassays, hormone measurements, detection of cardiology markers, detection of cancer markers, detection of infectious disease agents, etc. These tests may be carried out in an assay chamber of the device.

Preferred features of an embodiment are as for other embodiments mutatis mutandis.

Referring to FIGS. 1-4, a device 1 is partially shown. Device 1 may have a top (major) surface 2, and an end (minor) surface 3 and respective side surfaces 4. The bottom surface of the device cannot be seen. Device 1 tapers towards end surface 3. In some embodiments, device 1 does not have this taper and, in others, it may have a hammerhead shape. A sample-receiving chamber 5, defined at least in part by surface S, may be recessed in the device 1 such that it opens into top surface 2 and end surface 3. In an alternative embodiment, sample-receiving chamber 5 opens into top surface 2 and a side surface 4.

The sample receiving chamber 5 may have an inlet end, and an outlet end (having width Y) which opens into a conduit 6. The inlet end may be substantially larger than the outlet end such that the width W of chamber 5 tapers towards to the outlet end in a V-shape. Alternative generally V- or U-shaped chambers are shown in FIGS. 5a and b. In one embodiment, sample receiving chamber 5 tapers such that the dimension A decreases in value from the inlet end to the outlet end. In general, the sample chamber may be of any shape and dimensions so long as a liquid sample is able to pass from the inlet end to the outlet end by capillary action. In order to speed the passage of fluid within the chamber, the shape and dimensions of the chamber may be chosen such that the capillarity at the outlet end is greater than the capillarity at the inlet end. A conduit axis 10 may be defined along the conduit. The sample-receiving surface may be outwardly exposed along an axis 11 perpendicular to the conduit axis.

As shown in the Figures, conduit 6 is a channel which may be recessed into the top surface 2. Although not shown, conduit 6 may be closed by means of a laminar layer laid onto top surface 2. The layer may overlay all or a part of the sample-receiving chamber 5, although it is not preferred if it overlays all of sample-receiving chamber 5 because the additional friction provided by the layer over the chamber 5 reduces the speed at which liquid can travel down conduit 6. Partial overlay of the sample-receiving chamber 5 may be advantageous to break the surface tension of the sample as it is applied to the sample receiving chamber and aid entry of the sample into conduit 6. Partial overlay also allows for the addition of a sample volume that is larger than could be added to sample receiving chamber that is overlayed. The other end of conduit 6 leads to an area of the device where an analysis or assay of the liquid can be carried out (not shown).

In one embodiment, dimension A may be 0.9 mm, B may be 2.5 mm, C may be 0.2 mm, D may be 3 mm and E may be 0.2 mm.

Devices can be prepared using a variety of techniques known in the art. For example, injection molding or micro-injection molding using suitable molds can be used. Alternatively, embossing techniques where the structure may be pressed into a material and techniques using silicon etching and/or photolithography can also be used.

Figure 7:
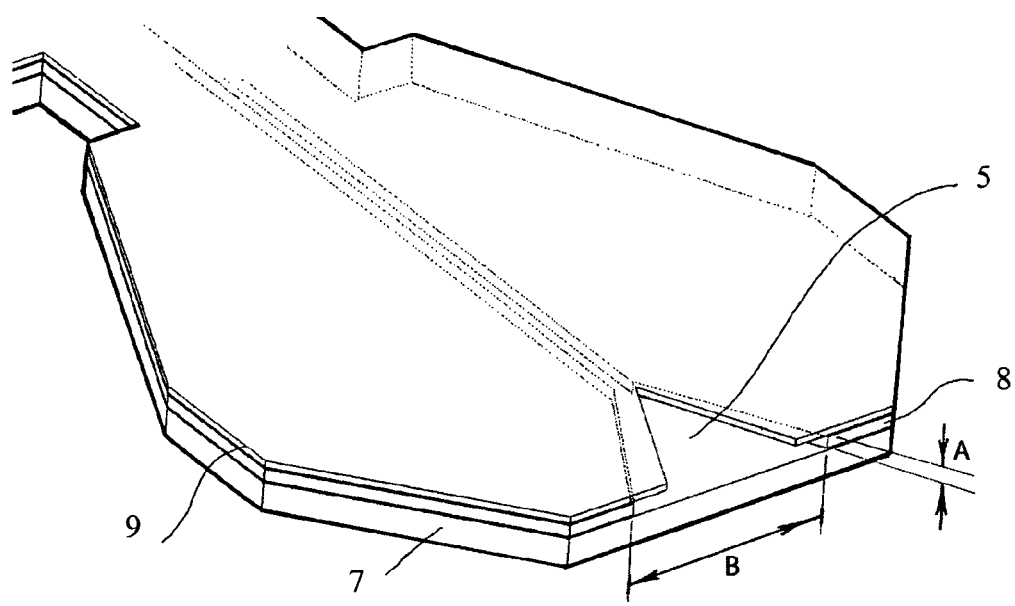
FIG. 7 is a partial isometric view of the front end of another embodiment of the invention.
Figure 8:
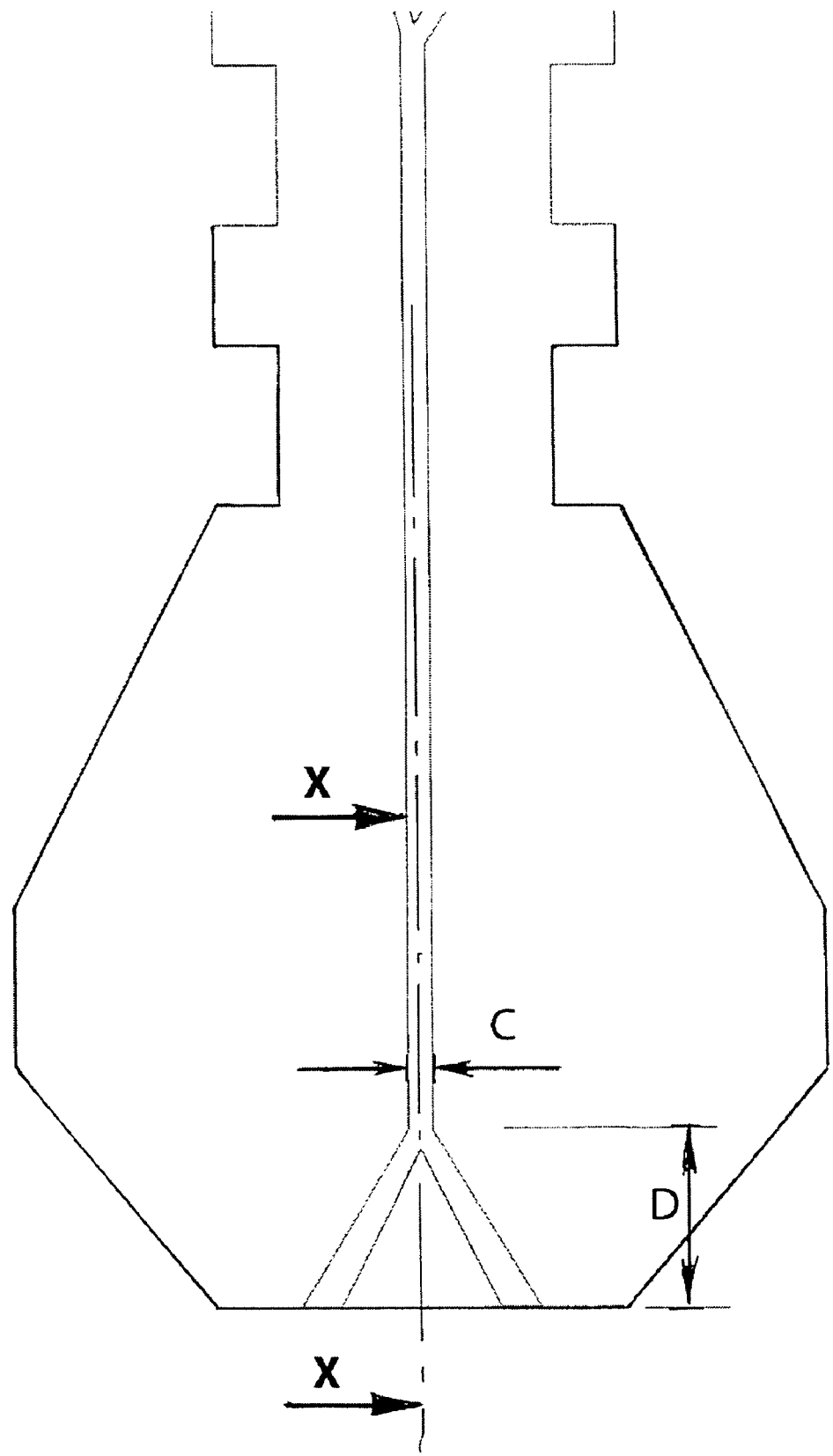
FIG. 8 is a plan view of the device of FIG. 7.
Figure 9:
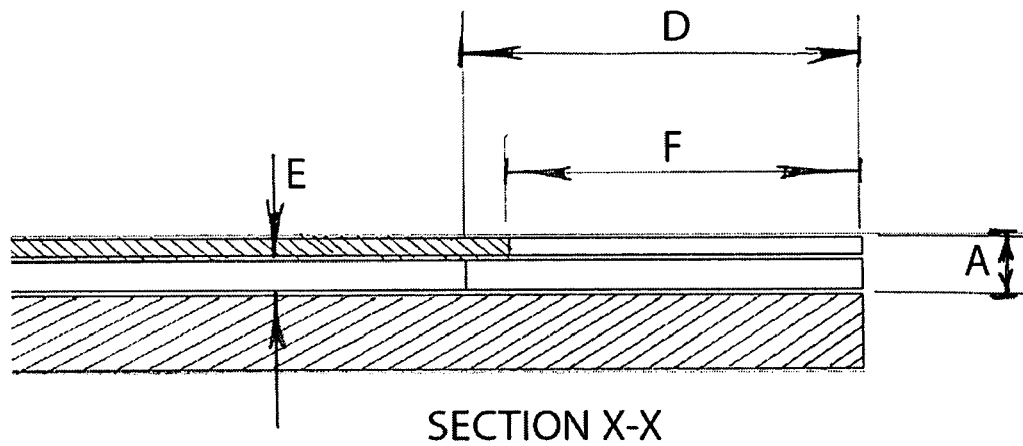
FIG. 9 is a section along line X-X in FIG. 8.

As yet a further alternative, the device may be made by laminating two or more layers. Referring to FIG. 7, such a device may comprise three layers. In the depicted embodiment, a base layer 7 forms the bottom surface of the chamber 5 and channel 6. A middle layer 8 has cuts therethrough to form the walls of the chamber 5 and channel 6. A top layer 9 forms the top surface of the channel 6. In the illustrated embodiment, top layer 9 partially overlays the sample receiving chamber 5 that is formed by the cut sides of layer 8 and the top surface of base layer 7. A plan view of FIG. 7 is shown in FIG. 8 and a section along line X-X of FIG. 8 is shown in FIG. 9.

In one embodiment, dimension A is 0.275 mm, B is 3 mm, C is 0.3 mm, D is 2.5 mm, E is 0.175 mm and F is 2 mm.

A laminated device in accordance with the present invention may be made as is described in UK Patent Application No. 0327094.9, the disclosure of which is incorporated by reference.

EXAMPLE

Polystyrene devices were injection molded with a sample-receiving chamber as shown in FIGS. 1-4. These devices were then treated with plasma enhanced chemical vapor deposition to coat the surface with a hydrophilic molecular layer such that the contact angle following treatment was approximately 11°. Techniques for doing this are well known to those skilled in the art. The devices were then laminated with a hydrophilic laminate (contact angle 11°) such that the laminate covered the conduit 6, but not the sample-receiving chamber 5.

Various volumes of fresh whole blood were pipetted onto the sample-receiving chamber 5 (blood from a finger prick source can also be applied directly to the sample-receiving chamber). The time taken for the blood to travel down the conduit 6 to a fixed point was determined. The measurements are listed in Table 1. These fill times plotted against the volume of whole blood added to the device are shown in FIG. 6.

It can be seen that volumes of 5 µl or less result in fill times of greater than about 20 seconds, and volumes of 7 µl or more have little effect on fill time.

TABLE 1

| Blood Volume Pipetted (µl) | Fill Time (seconds) |
| --- | --- |
| 4.5 | 33.4 |
| 4.75 | 21.7 |
| 5 | 17 |
| 5 | 16.9 |
| 6 | 16.6 |
| 6 | 15.7 |
| 7 | 13.8 |
| 7 | 12.4 |
| 10 | 12.6 |

The invention claimed is:

1. A device for receiving a sample of liquid, comprising:
   a body comprising opposed first and second major external surfaces each defining a periphery, and a peripheral wall joining the peripheries of the major surfaces;
   a conduit extending from an outlet of a sample-receiving recess into an interior of the body between the first and second major surfaces, the conduit being arranged so as to allow the liquid to pass from the outlet into the conduit by capillary action, and the conduit defining a conduit axis that runs along its length; and
   the sample-receiving recess located in the body adjacent to the periphery of the first major surface of the body, the recess having a lower surface and an inlet, the lower surface being disposed on an opposite side of the conduit axis from the first major surface, being substantially parallel to the first major surface and being outwardly exposed along an axis perpendicular to the conduit axis, the inlet being defined in part by the peripheral wall of the first major surface, the outlet being spaced apart from the peripheral wall of the first major surface within the body, and a width of the recess decreasing from the inlet to the outlet, a maximum width of the conduit no greater than a minimum width of the recess.

2. A device as claimed in claim 1, wherein the body is a generally rectilinear strip, or is wedge- or disc-shaped.

3. A device as claimed in claim 2, wherein the peripheral wall is an end or side wall of the body and one of the major surfaces is a top surface of the body.

4. A device as claimed in claim 1, wherein the body is generally cylindrical.

5. A device as claimed in claim 4, wherein the peripheral wall is an end wall and the first and second major surfaces are respective halves of an outer surface of a cylinder.

6. A device as claimed in claim 1, wherein the sample-receiving recess tapers in at least one dimension from the inlet to the outlet.

7. A device as claimed in claim 6, wherein the sample-receiving recess is generally V- or U-shaped.

8. A device as claimed in claim 6, wherein the sample-receiving recess tapers continuously from the inlet end to the outlet end.

9. A device as claimed in claim 6, wherein the sample-receiving recess tapers continuously in two dimensions from the inlet end to the outlet end.

10. A device as claimed in claim 1, wherein the sample-receiving recess and the conduit are coated with a hydrophilic coating, providing a contact angle of 90 degrees or less.

* * * * *